(12) United States Patent
Hartstra

(10) Patent No.: US 10,231,868 B2
(45) Date of Patent: Mar. 19, 2019

(54) EYE SURGICAL CUTTING TOOL

(71) Applicant: D.O.R.C. Dutch Ophthalmic Research Center (International) B.V., Zuidland (NL)

(72) Inventor: Andre Hartstra, Zuidland (NL)

(73) Assignee: D.O.R.C. Dutch Ophtalmic Research Center (International) B.V., Zuidland (NL)

( * ) Notice: Subject to any disclaimer, the term of this patent is extended or adjusted under 35 U.S.C. 154(b) by 287 days.

(21) Appl. No.: 14/775,593

(22) PCT Filed: Mar. 13, 2014

(86) PCT No.: PCT/NL2014/050152
§ 371 (c)(1),
(2) Date: Sep. 11, 2015

(87) PCT Pub. No.: WO2014/142663
PCT Pub. Date: Sep. 18, 2014

(65) Prior Publication Data
US 2016/0022489 A1 Jan. 28, 2016

(30) Foreign Application Priority Data

Mar. 13, 2013 (NL) ...................................... 2010444

(51) Int. Cl.
*A61F 9/007* (2006.01)
*A61B 17/3205* (2006.01)
*A61B 17/32* (2006.01)

(52) U.S. Cl.
CPC ...... *A61F 9/00736* (2013.01); *A61F 9/00763* (2013.01); *A61B 2017/320028* (2013.01); *A61B 2217/005* (2013.01); *A61F 2230/0069* (2013.01)

(58) Field of Classification Search
CPC ............ A61B 10/0233; A61B 10/0266; A61B 10/0275; A61B 10/0283; A61B 17/32;
(Continued)

(56) References Cited

U.S. PATENT DOCUMENTS 3,815,604 A * 6/1974 O'Malley ............... A61B 18/12
604/22
4,011,869 A * 3/1977 Seiler, Jr. ............ A61F 9/00763
604/22
(Continued)

FOREIGN PATENT DOCUMENTS

DE 10 2010 050 337 5/2012
JP H3-39155 A 2/1991
(Continued)

OTHER PUBLICATIONS

International Search Report and Written Opinion issued in PCT/NL2014/050152, dated May 21, 2014.
(Continued)

*Primary Examiner* — Ryan J Severson
(74) *Attorney, Agent, or Firm* — Knobbe, Martens, Olson & Bear, LLP

(57) ABSTRACT

An eye surgical cutting tool includes a tubular outer part and an axially movable tubular inner part arranged in the outer part. The outer part has a closed distal end, and the inner part has an open distal end. Both parts have an opening in the tube. Both openings are bounded on the distal side by a distal cutting edge in the respective tube. The axial position of the distal cutting edge of the inner part as a function of the circumferential direction initially proceeds towards the proximal end, and then back to the distal end again. The tool is provided with suction means to have, during use of the cutting tool, ocular tissue extended through the opening of the outer part into the interior of the outer part and to convey
(Continued)

severed tissue via the interior of the inner part to a proximal end of the inner part.

10 Claims, 3 Drawing Sheets

(58) Field of Classification Search
CPC ...... A61B 17/320016; A61B 17/32002; A61B 17/3205; A61B 17/32053; A61B 2010/0208; A61B 2010/0225; A61B 2017/320024; A61B 2017/320028; A61B 2017/320032; A61B 2217/005; A61F 9/007; A61F 9/00709; A61F 9/00736; A61F 9/00745; A61F 9/00754; A61F 9/00763; A61F 9/013; A61F 9/0133
See application file for complete search history.

(56) References Cited

U.S. PATENT DOCUMENTS

| | | | | |
|---|---|---|---|---|
| 4,099,529 A * | 7/1978 | Peyman | ............... | A61F 9/00763 30/241 |
| 4,111,207 A * | 9/1978 | Seiler, Jr. | ............ | A61F 9/00763 30/241 |
| 4,210,146 A * | 7/1980 | Banko | ................. | A61F 9/00763 30/241 |
| 4,577,629 A * | 3/1986 | Martinez | ............. | A61F 9/00763 604/22 |
| 4,811,734 A * | 3/1989 | McGurk-Burleson | ....................... | A61B 17/32002 30/240 |
| 5,019,035 A * | 5/1991 | Missirlian | ........... | A61F 9/00763 604/22 |
| 5,047,008 A * | 9/1991 | de Juan, Jr. | ......... | A61F 9/00763 600/564 |
| 5,106,364 A | 4/1992 | Hayafuji et al. | | |
| 5,385,570 A | 1/1995 | Chin et al. | | |
| 5,458,112 A | 10/1995 | Weaver | | |
| 5,582,618 A * | 12/1996 | Chin | ................. | A61B 17/1611 606/170 |
| 5,630,827 A * | 5/1997 | Vijfvinkel | .......... | A61B 10/0266 604/22 |
| 5,782,849 A | 7/1998 | Miller | | |
| 5,843,111 A * | 12/1998 | Vijfvinkel | .......... | A61B 10/0266 604/22 |
| 6,258,111 B1 * | 7/2001 | Ross | ................. | A61B 17/32002 606/171 |
| 6,485,499 B1 * | 11/2002 | Oberkamp | .......... | A61F 9/00763 606/171 |
| 6,514,268 B2 * | 2/2003 | Finlay | ................. | A61F 9/00763 606/170 |
| 6,695,821 B1 * | 2/2004 | Sjaarda | ............... | A61M 3/0279 604/264 |
| 6,709,408 B2 * | 3/2004 | Fisher | ................ | A61B 10/0266 600/562 |
| 6,743,245 B2 * | 6/2004 | Lobdell | .............. | A61F 9/00763 600/565 |
| 6,773,445 B2 * | 8/2004 | Finlay | ................ | A61F 9/00763 606/170 |
| 6,872,185 B2 * | 3/2005 | Fisher | ................ | A61B 10/0266 600/562 |
| 6,890,309 B2 * | 5/2005 | Fisher | ................ | A61B 10/0266 600/562 |
| 6,908,440 B2 * | 6/2005 | Fisher | ................ | A61B 10/0266 600/562 |
| 8,298,253 B2 * | 10/2012 | Charles | ............... | A61F 9/00763 604/22 |
| 8,313,501 B2 * | 11/2012 | Miller | .................... | A61B 17/32 606/171 |
| 8,608,753 B2 * | 12/2013 | Luloh | ................ | A61F 9/00763 606/107 |
| 8,784,432 B2 * | 7/2014 | Gagnepain | .......... | A61F 9/00763 606/107 |
| 8,808,318 B2 * | 8/2014 | Auld | ................... | A61F 9/00763 604/22 |
| 8,845,666 B2 * | 9/2014 | Underwood | ..... | A61B 17/32002 606/171 |
| 9,060,841 B2 * | 6/2015 | McCawley | ......... | A61F 9/00763 |
| 9,603,740 B2 * | 3/2017 | Fantoni | ............... | A61F 9/00763 |
| 9,615,969 B2 * | 4/2017 | Nissan | ............... | A61F 9/00763 |
| 2004/0049217 A1 * | 3/2004 | Ross | ................ | A61B 17/32002 606/171 |
| 2005/0090765 A1 * | 4/2005 | Fisher | ................ | A61B 10/0266 600/570 |
| 2006/0004397 A1 * | 1/2006 | Osawa | ............... | A61F 9/00736 606/180 |
| 2006/0271082 A1 * | 11/2006 | Kirchhevel | ...... | A61B 17/32002 606/170 |
| 2007/0185514 A1 * | 8/2007 | Kirchhevel | ......... | A61F 9/00763 606/171 |
| 2008/0154292 A1 * | 6/2008 | Huculak | ............. | A61F 9/00763 606/167 |
| 2008/0208233 A1 * | 8/2008 | Barnes | ................ | A61F 9/00763 606/171 |
| 2009/0069831 A1 * | 3/2009 | Miller | .................... | A61B 17/32 606/171 |
| 2009/0157111 A1 * | 6/2009 | Goh | ................. | A61B 17/32002 606/171 |
| 2009/0281479 A1 * | 11/2009 | Gagnepain | .......... | A61F 9/00763 604/22 |
| 2010/0152762 A1 * | 6/2010 | Mark | ............... | A61B 17/32002 606/180 |
| 2010/0312169 A1 * | 12/2010 | Auld | ................... | A61F 9/00763 604/22 |
| 2011/0295296 A1 * | 12/2011 | Charles | ............... | A61F 9/00763 606/171 |
| 2012/0158030 A1 * | 6/2012 | Underwood | ..... | A61B 17/32002 606/171 |
| 2012/0221033 A1 * | 8/2012 | Auld | ................... | A61F 9/00763 606/170 |
| 2013/0053759 A1 * | 2/2013 | McCawley | ......... | A61F 9/00763 604/22 |
| 2013/0211439 A1 * | 8/2013 | Geuder | ............ | A61B 17/32002 606/171 |
| 2014/0296900 A1 * | 10/2014 | Barnes | ................ | A61F 9/00763 606/171 |
| 2014/0364885 A1 * | 12/2014 | Wells | ................... | A61F 9/00754 606/170 |
| 2015/0182379 A1 * | 7/2015 | Fantoni | ............... | A61F 9/00763 606/171 |
| 2015/0335485 A1 * | 11/2015 | Rieger | ............... | A61F 9/00763 606/171 |
| 2016/0022489 A1 * | 1/2016 | Hartstra | ............. | A61F 9/00763 606/166 |

FOREIGN PATENT DOCUMENTS

WO 01/30281 A1 5/2001
WO 2004/002337 A1 1/2004

OTHER PUBLICATIONS

Stanislao Rizzo, M.D, "Performance of a Modified Vitrectomy Probe in Small-gauge Vitrectomy," Retina Today, Sep. 2011, pp. 40-42.
Lima, Luiz H., et al., "A New Dual Port Cutter System for Vitrectomy Surgery", Retina, The Journal of Retinal and Vitreous Diseases, 2010, 30:9, pp. 1515-1519.

* cited by examiner

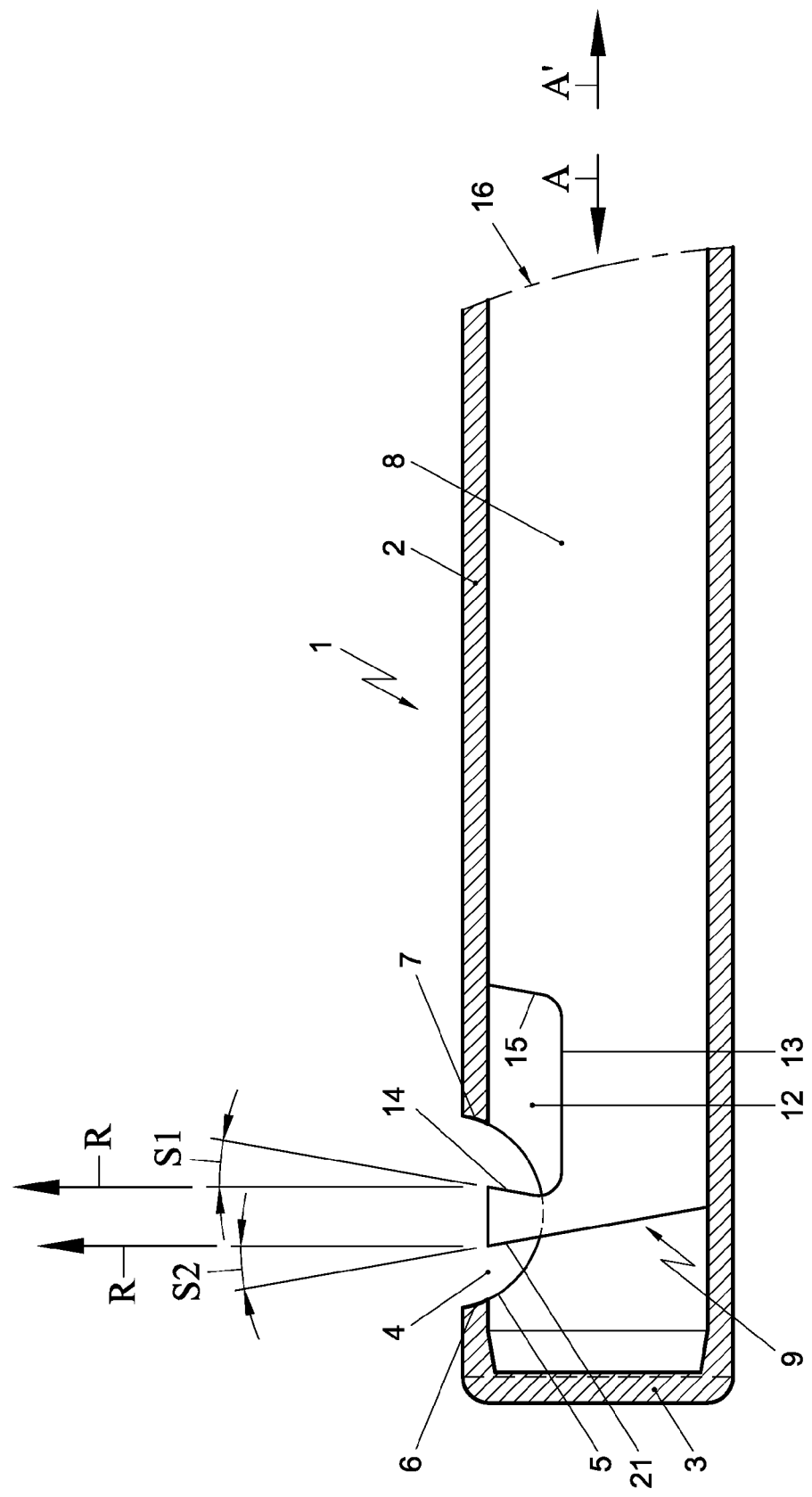

EYE SURGICAL CUTTING TOOL

CROSS REFERENCE TO RELATED APPLICATIONS

This application is the U.S. National Phase of International Application No. PCT/NL2014/050152, filed Mar. 13, 2014, designating the U.S. and published in English as WO 2014/142663 on Sep. 18, 2014 which claims the benefit of Netherlands Patent Application No. 2010444, filed Mar. 13, 2013.

FIELD OF THE INVENTION

The invention relates to an eye surgical cutting tool, comprising a tubular outer part with a closed distal end and an opening in the tube of the outer part, near the closed end, the opening being bounded by an edge profile formed in the tube which has a distal cutting edge and an opposite proximal cutting edge, furthermore comprising a tubular inner part which has an open distal end and is arranged in the tubular outer part so as to be movable in an axial direction, additionally comprising suction means to have, during use of the cutting tool, ocular tissue extend through the opening of the outer part into the interior of the outer part and to convey severed tissue via the interior of the inner part to a proximal end of the inner part, wherein the tube of the inner part also has an opening, near the open end and bounded by an edge profile formed in the tube with a distal cutting edge and an opposite proximal edge, such that the opening of the outer part and the opening of the inner part are mutually aligned in a circumferential direction around the outer part and in an aligned axial position of the inner part with respect to the outer part.

Such an eye surgical cutting tool is known as a vitrectomy cutter with a double cutting or scissor movement. During a cycle in which the inner part performs a back-and-forth movement in the outer part, a cutting or scissor movement takes place twice. A first cutting or scissor movement is realized by cooperation of the distal end of the inner part with the distal cutting edge of the outer part. A second cutting or scissor movement comes about through cooperation of the distal cutting edge of the inner part with the proximal cutting edge of the outer part.

SUMMARY

The invention contemplates providing an eye surgical cutting tool of the kind mentioned in the opening paragraph hereof, with the functionality thereof augmented. To this end, the edge profile of the opening in the inner part is shaped such that the axial position of the distal cutting edge as a function of the circumferential direction of the inner part initially proceeds towards the proximal end and then proceeds back to the distal end.

According to an aspect, the distal cutting edge of the inner part is designed with a specific profile whereby a part located nearer to the proximal end is situated between parts that are located nearer to the distal end, for instance by providing the profile with a segment which, viewed in a longitudinal section of the cutting tool, makes an angle with respect to the body axis of the inner part. The angle mentioned is between 0° and 90°, preferably between about 20° and about 70°, more preferably between about 30° and about 60°, for instance about 45°. Thus, on the distal cutting edge a cutting face is formed which leans over to the proximal end of the inner part. This creates an improved cutting action in the above-mentioned second cutting or scissor movement. In fact, the intervening ocular tissue can thus be engaged more effectively. Also, what is thus achieved is that the tissue is cut off or snipped off not approximately simultaneously, but from the part located nearer to the proximal end towards both sides, viewed in circumferential direction, which further promotes the effectiveness of the cutting or scissor movement. Owing to the increased cutting and snipping capacity the surgical intervention can be shortened. Moreover, the traction on the ocular tissue to be removed decreases while the suction flow increases.

BRIEF DESCRIPTION OF THE DRAWINGS

The invention will be further elucidated on the basis of exemplary embodiments which are represented in the drawing. In the drawing:

FIG. 3 shows a schematic view of a longitudinal section of another eye surgical cutting tool according to the invention.

DETAILED DESCRIPTION OF CERTAIN EMBODIMENTS

Figure 1A:
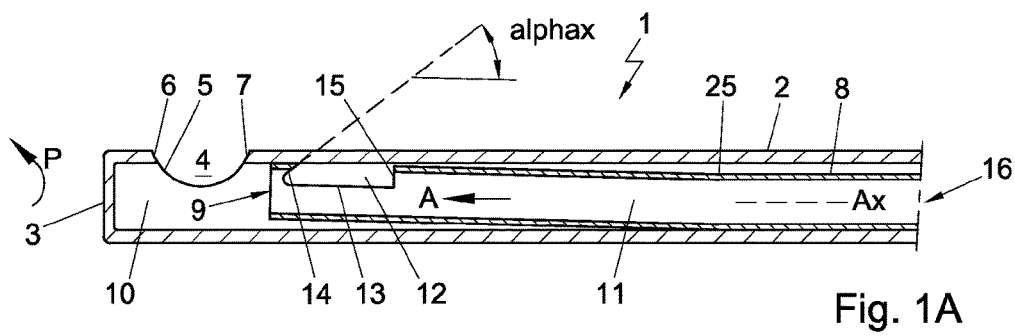
FIG. 1a shows a schematic view of a longitudinal section of an eye surgical cutting tool according to the invention in a first condition.

The drawing merely shows a schematic representation of preferred embodiments of the invention. In the figures, like or corresponding parts are denoted with the same reference numerals.

FIG. 1a shows an eye surgical cutting tool 1 according to the invention, in a first condition. The cutting tool 1 has a tubular outer part 2 and a tubular inner part 8 which is arranged in the tubular outer part 2 so as to be movable in an axial direction A.

The tubular outer part 2 is provided with a closed distal end 3 and an opening 4 in the tube of the outer part, near the closed end 3. The opening 4 is bounded by an edge profile 5, formed in the tube 2, which has a distal cutting edge 6 and an opposite proximal cutting edge 7. The tubular inner part 8 is provided with an open distal end 9.

Furthermore, the eye surgical cutting tool 1 has suction means to have ocular tissue to be severed, during use of the cutting tool 1, extend through the opening 4 of the outer part 2 into the interior 10 of the outer part 2. The suction means are further arranged to convey severed tissue via the interior 11 of the inner part 8 to a proximal end 16 of the inner part 8, for further discharge.

The tube 8 of the inner part, like the outer part 2, has an opening 12, near the open end 9 and bounded by an edge profile 13, formed in the tube 2, with a distal cutting edge 14 and an opposite proximal edge 15. The openings 4, 12 of the outer part 2 and the inner part 8 are mutually aligned in a circumferential direction P around the outer part 2. Moreover, the openings 4, 12 are aligned in the axial direction A when the inner part 8 is in a specific axial position with respect to the outer part 2 in which the openings 4, 12 are centered with respect to each other. This specific axial position is also called the aligned axial position of the inner part 8.

During operation of the eye surgical cutting tool 1 the inner part 8 performs back-and-forth movements within the outer part 2, in the axial direction A. Ocular tissue is drawn into the outer part 2 and then severed. FIGS. 1*a-d* show successive positions of the inner part 8 during a single cycle.

In the first condition as shown in FIG. 1*a*, the inner part 8 is in a proximal position. The opening 4 of the outer part 2 is then between the distal end 3 of the outer part 2 and the distal end 9 of the inner part 8. Through the operation of the suction means, a reduced pressure is created in the interior 10 of the outer part, so that ocular tissue can be drawn in via the opening 4. During this first aspiration phase, the drawn-in ocular tissue then extends into the interior 10 of the outer part 2.

Figure 1B:
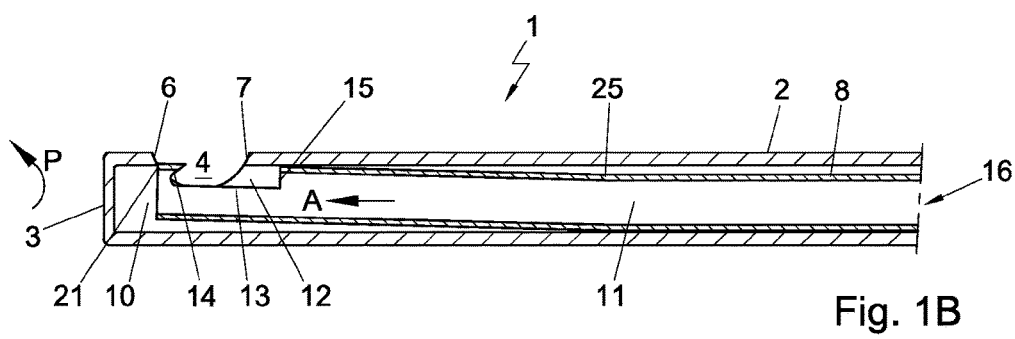
FIG. 1b shows a schematic view of a longitudinal section of the eye surgical cutting tool of FIG. 1a in a second condition.

FIG. 1*b* shows a schematic view of a longitudinal section of the eye surgical cutting tool 1 in a second condition. The inner part 8 has been moved from the proximal position along the axial direction A in the direction of the distal end 3 of the outer part 2 to a first intermediate position, so far that the distal end 9 of the inner part 8 is near the distal cutting edge 6 of the edge profile 5 of the outer part 2. The edge of the distal end 9 of the inner part 8 forms a distal cutting edge 21. By moving the inner part 8 along the distal cutting edge 6 of the outer part 2 a cutting or scissor movement occurs at the ocular tissue that is clamped between the edge profile 5 of the opening 4 in the outer part 2 on the one hand and the distal end 9 of the inner part 8 on the other hand.

The cut-off or snipped-off tissue is discharged by the suction means via the interior 11 of the inner part 8.

In the first intermediate position, as shown in FIG. 1*b*, likewise, ocular tissue can be drawn in, now via the opening 4 of the outer part 2 and via the opening 12 of the inner part 8. The ocular tissue that is drawn in during this second aspiration phase will be cut off or snipped off in a later phase of the back-and-forth movement of the inner part 8, as described below.

Figure 1C:
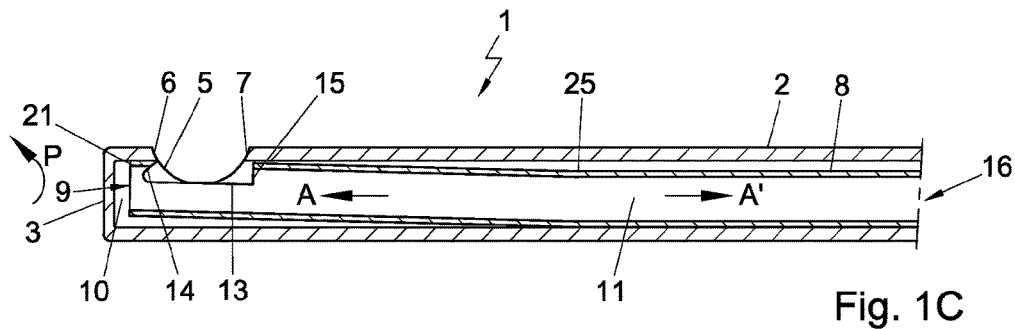
FIG. 1c shows a schematic view of a longitudinal section of the eye surgical cutting tool of FIG. 1a in a third condition.

FIG. 1*c* shows a schematic view of a longitudinal section of the eye surgical cutting tool 1 in a third condition. Now, the inner part has moved along the axial direction A from the first intermediate position, shown in FIG. 1*b*, to a distal position in which the distal end 9 of the inner part 8 is positioned near the distal end 3 of the outer part 2. The inner part 8 is now situated in the above-mentioned specific axial position with respect to the outer part 2 in which the openings 4, 12 are aligned with respect to each other. The above-described second aspiration phase still continues, so that the ocular tissue is drawn in via the openings 4, 12 of the outer part 2 and the inner part 8.

Figure 1D:
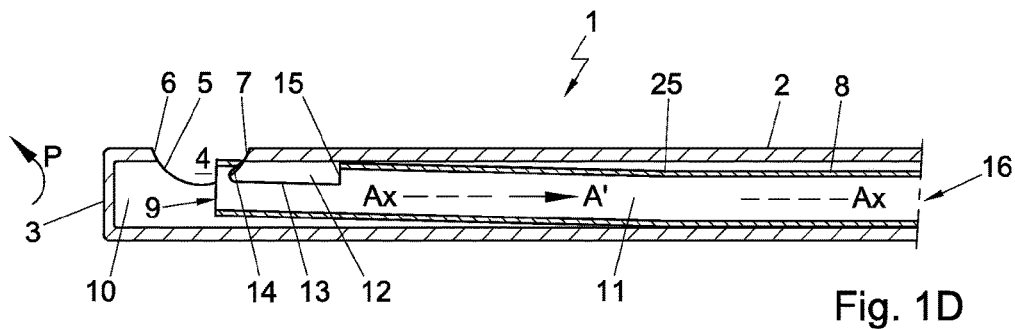
FIG. 1d shows a schematic view of a longitudinal section of the eye surgical cutting tool of FIG. 1a in a fourth condition.

FIG. 1*d* shows a schematic view of a longitudinal section of the eye surgical cutting tool 1 in a fourth condition. The inner part 8 has undergone a displacement from the distal position, shown in FIG. 1*c*, in an axial direction A' opposite to the above-mentioned axial direction A, to a second intermediate position, so far that the distal cutting edge 14 of the edge profile 13 of the inner part 8 is near the proximal cutting edge 7 of the edge profile 5 of the outer part 2. By moving the inner part 8 along the proximal cutting edge 7 of the outer part 2, again a cutting or scissor movement is created at the ocular tissue clamped between the edge profile 5 of the opening 4 in the outer part 2 on the one hand and the edge profile 13 of the inner part 8 on the other.

In this second intermediate position, as shown in FIG. 1*d*, once again, ocular tissue can be drawn in, now via the opening 4 of the outer part 2 into the interior 10 of the outer part 2, just as in the above-described first condition, in which the inner part 8 is in the proximal position, as shown in FIG. 1*a*. The ocular tissue that is drawn in during this aspiration phase will be cut off or snipped off in a new cycle of the back-and-forth movement of the inner part 8, viz., during the second condition as described with reference to FIG. 1*b*.

After the second intermediate position, the inner part 8 reaches the proximal position as shown in FIG. 1*a*, and the cycle of the back-and-forth movement repeats itself.

Thus, during a single cycle two aspiration phases occur. Also, in one cycle, a cutting or scissor movement is carried out twice, which is of benefit to the effectiveness of the eye surgical cutting tool.

Figure 2:
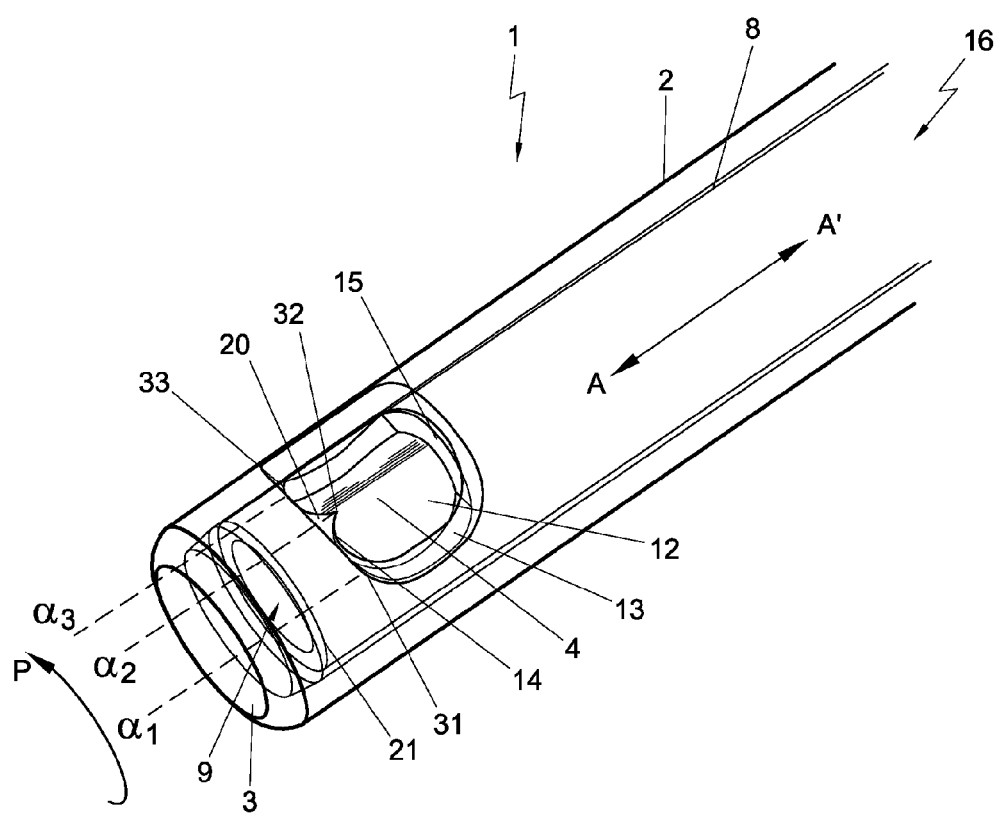
FIG. 2 shows a schematic perspective view of the eye surgical cutting tool of FIG. 1a, partly cutaway.

FIG. 2 shows a schematic perspective view of the eye surgical cutting tool 1 of FIG. 1*a* with the tool partly cutaway.

As shown in the figures, the axial position of the distal cutting edge 14 of the inner part 8 varies as a function of the circumferential direction of the inner part 8 which practically coincides with the circumferential direction P of the outer part 2. The cutting edge 14 is provided with a segment which, viewed in a longitudinal section of the cutting tool, makes an angle alphax with respect to the body axis Ax of the inner part 2. See, for instance, FIG. 1*a*. This angle alphax is between 0° and 90°, preferably between about 20° and about 70°, more preferably between about 30° and about 60°, for instance about 45°. Thus, on the distal cutting edge 14 a cutting face is formed which leans over with the cutting edge towards the proximal end 16 of the inner part 2. As shown in particular in FIG. 2, the distal cutting edge 14, starting from a first circumferential angle alpha 1 corresponding to a first axial position 31, initially proceeds in the direction of the proximal end 16. At a second circumferential angle alpha 2 of the distal cutting edge 14, corresponding to a second axial position 32, the distal cutting edge 14 is at a minimum distance with respect to the proximal end 16, and at a maximum distance with respect to the distal end 9 of the inner part 8. After that, the cutting edge 14 proceeds away from the proximal end 16 again. At a third circumferential angle alpha 3 of the distal cutting edge 14, corresponding to a third axial position 33, the distance with respect to the proximal end 16 has increased again and the distance with respect to the distal end 9 has decreased again.

Accordingly, the axial position of the distal cutting edge 14 initially proceeds towards the proximal end 16, and then back towards the distal end 9. Viewed along the axial direction A, the axial position of the cutting edge 14 first decreases and then increases again.

Owing to the specific design of the distal cutting edge, the ocular tissue is first pricked, as it were, whereupon the cutting or scissor movement is continued laterally in both circumferential directions until the ocular tissue is fully cut through.

Preferably, the distal cutting edge 14 is symmetrically shaped, as shown in FIG. 2. In principle, however, the cutting edge could also be made of non-symmetrical design.

As shown in FIG. 2, the axial position of the distal cutting edge 14 of the inner part 8 reaches an extremity about halfway in the range of the circumferential direction. Formulated differently, the cutting edge has a local minimum, viewed in the axial direction A. Thus, the axial distance between the distal cutting edge 14 of the inner part 8 on the one hand and the proximal end 16 of the inner part 8 on the other hand reaches a minimum approximately halfway in the range of the cutting edge 14, viewed in the circumferential direction P. The cutting edge first proceeds towards the proximal end 16 and, after reaching the axial minimum, proceeds away from the proximal end 16 again. By designing the distal cutting edge 14 with a tooth profile that is directed to the proximal end 16, an improved cutting or snipping operation can be carried out. The tooth profile can contain a single tooth 20 or a plurality of teeth. A tooth may be pointed, as shown, or have a different shape, such as a segment of a circle.

As shown in FIGS. 1*a*-1*d*, the tube of the inner part 8 is not straight, but exhibits a slight kink 25, so that the inner part 8 during the back-and-forth movement exerts a force on the inner shaft of the outer part 2. By providing the tube of the inner part 8 with a slight kink or slight bend, the cutting or shearing effect improves still further. A change of the local orientation of the tube can be realized during manufacture by deformation of a straight tube. However, the inner part 8 could also be designed to be wholly or substantially straight, i.e., with a rectilinear body axis Ax.

FIG. 3 shows a schematic view of a longitudinal section of another eye surgical cutting tool 1 according to the invention. As in the embodiment described above, the distal cutting edge 14 of the edge profile 13 of the inner part 8 does not extend transversely to the body axis Ax of the inner part 8, but slightly obliquely thereto. The distal cutting edge 14 of the edge profile 13 leans over towards the proximal end 16 of the inner part 8. The cutting face formed by the distal cutting edge 14 preferably makes an angle of between about 20° and about 70° with respect to the body axis Ax of the inner part 8. This cutting face is also referred to as the proximal cutting face. Consequently, the angle S1 of the proximal cutting face with respect to a radial direction R, transverse to the body axis Ax of the inner part 8, is preferably also between about 20° and about 70°. It is noted that the angle S1 of the proximal cutting face with respect to the radial direction R can also be less than 20°, for instance between about 5° and about 20°.

The distal end 9 forms a distal cutting face and, in the embodiment shown in FIG. 3, is likewise oblique with respect to the radial direction R, though tilted the other way than is the proximal cutting face. Thus the distal cutting face leans away from the proximal end 16 of the inner part 8. The angles S1, S2 included by the proximal and distal cutting faces with respect to the radial direction R are preferably of approximately equal magnitude, so that the cutting and snipping action during the back-and-forth movement of the inner part 8 is comparable.

Thus, both cutting edges of the inner part, i.e., the distal cutting edge 14 of the edge profile 13 and the distal cutting edge of the open distal end 9, form cutting faces with opposite angles of tilt S1, S2 with respect to the radial direction R. The cutting faces face away from each other, viewed from the body axis Ax of the inner part 8. In a specific embodiment, the angles of tilt S1, S2 are of approximately equal magnitude. By use of the above-described cutting tools, tissue can be cut and/or snipped faster, since there are two cutting or snipping operations per cycle. Also, operation is safer since the chance of laceration of the tissue is considerably reduced. Furthermore, a continuous aspiration can be applied, which results in an improved flow action. This also improves the action of the cutting tool.

The invention is not limited to the exemplary embodiments described here. Many variants are possible.

Thus, the suction means can comprise a pump which is connectable to the proximal end of the inner part to realize a reduced pressure that draws ocular tissue into the outer part and carries it off after the cutting or snipping operation via the proximal end of the inner part.

Such variants will be clear to those skilled in the art and are understood to be within the scope of the invention, as set forth in the appended claims.

What is claimed is:

1. An eye surgical cutting tool, comprising:
   a tubular outer part with a closed distal end and an opening in the tube of the outer part, near the closed end, the opening being bounded by an edge profile formed in the tube which has a distal cutting edge and an opposite proximal cutting edge,
   a tubular inner part which has an open distal end and is arranged in the tubular outer part so as to be movable in an axial direction, and
   a suction that is configured to, during use of the cutting tool, extend ocular tissue through the opening of the outer part into the interior of the outer part and convey severed tissue via the interior of the inner part to a proximal end of the inner part,
   wherein the tube of the inner part also has an opening, near the open end and bounded by an edge profile formed in the tube with a distal cutting edge and an opposite proximal edge, such that the opening of the outer part and the opening of the inner part are mutually aligned in a circumferential direction around the outer part and in an aligned axial position of the inner part with respect to the outer part, and
   wherein the open distal end of the inner part forms a distal cutting edge with a distal cutting face which is oblique relative to a body axis of the tubular inner part, the distal cutting face leaning away from the proximal end of the inner part, and wherein the distal cutting edge of the edge profile formed in the inner part forms a proximal cutting face which is oblique relative to the body axis of the tubular inner part, the proximal cutting face leaning over towards the proximal end of the inner part.

2. The eye surgical cutting tool according to claim 1, wherein an angle between the proximal cutting face and a radial direction transverse to the body axis of the tubular inner part is between about 20° and about 70°.

3. The eye surgical cutting tool according to claim 1, wherein an axial distance between the distal cutting edge of the edge profile formed in the inner part on one hand and the proximal end of the inner part on the other hand reaches a minimum approximately halfway in the range of the distal cutting edge of the edge profile, viewed in circumferential direction.

4. The eye surgical cutting tool according to claim 1, wherein the distal cutting edge of the edge profile of the inner part has a tooth profile which is directed towards the proximal end.

5. The eye surgical cutting tool according to claim 1, wherein the inner part has a kink or bend.

6. The eye surgical cutting tool according to claim 1, wherein the distal cutting edges of the inner part form cutting faces with opposite angles of tilt.

7. The eye surgical cutting tool according to claim 6, wherein the angles of tilt are of approximately equal magnitude.

8. The eye surgical cutting tool according to claim 1, wherein the axial position of the distal cutting edge of the inner part as a function of the circumferential direction of the inner part initially proceeds towards the proximal end and then proceeds back to the distal end.

9. An eye surgical cutting tool, comprising:
a tubular outer part with a closed distal end and an opening in the tube of the outer part, near the closed end, the opening being bounded by an edge profile formed in the tube which has a distal cutting edge and an opposite proximal cutting edge,
a tubular inner part which has an open distal end and is arranged in the tubular outer part so as to be movable in an axial direction, and
a suction that is configured to, during use of the cutting tool, extend ocular tissue through the opening of the outer part into the interior of the outer part and to convey severed tissue via the interior of the inner part to a proximal end of the inner part,
wherein the tube of the inner part also has an opening, near the open end and bounded by an edge profile formed in the tube with a distal cutting edge and an opposite proximal edge, such that the opening of the outer part and the opening of the inner part are mutually aligned in a circumferential direction around the outer part and in an aligned axial position of the inner part with respect to the outer part, and
wherein the open distal end of the inner part forms a distal cutting edge with a distal cutting face which is oblique relative to a body axis of the tubular inner part, the distal cutting face leaning away from the proximal end of the inner part, and wherein the distal cutting edge of the edge profile formed in the inner part forms a proximal cutting face which is oblique relative to the body axis of the tubular inner part, the proximal cutting face leaning over towards the proximal end of the inner part, an angle between the proximal cutting face and a radial direction transverse to the body axis of the tubular inner part being between about 5° and about 70°.

10. An eye surgical cutting tool, comprising:
a tubular outer part with a closed distal end and an opening in the tube of the outer part, near the closed end, the opening being bounded by an edge profile formed in the tube which has a distal cutting edge and an opposite proximal cutting edge,
a tubular inner part which has an open distal end and is arranged in the tubular outer part so as to be movable in an axial direction, and
a suction that is configured to, during use of the cutting tool, extend ocular tissue through the opening of the outer part into the interior of the outer part and to convey severed tissue via the interior of the inner part to a proximal end of the inner part,
wherein the tube of the inner part also has an opening, near the open end and bounded by an edge profile formed in the tube with a distal cutting edge and an opposite proximal edge, such that the opening of the outer part and the opening of the inner part are mutually aligned in a circumferential direction around the outer part and in an aligned axial position of the inner part with respect to the outer part, and
wherein the open distal end of the inner part forms a distal cutting edge with a distal cutting face which is oblique relative to a body axis of the tubular inner part, the distal cutting face leaning away from the proximal end of the inner part, and wherein the distal cutting edge of the edge profile formed in the inner part forms a proximal cutting face which is oblique relative to the body axis of the tubular inner part, the proximal cutting face leaning over towards the proximal end of the inner part, the proximal cutting face having a tooth profile which is directed toward the proximal end, the tooth profile containing a single tooth.

* * * * *